US007524467B2

(12) United States Patent
Pohl

(10) Patent No.: US 7,524,467 B2
(45) Date of Patent: *Apr. 28, 2009

(54) PROCESS FOR THE PRODUCTION OF ALKYLBENZENE

(75) Inventor: Stephen L. Pohl, Wayne, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 428 days.

This patent is subject to a terminal disclaimer.

(21) Appl. No.: 11/449,548

(22) Filed: Jun. 8, 2006

(65) Prior Publication Data

US 2006/0229479 A1  Oct. 12, 2006

Related U.S. Application Data

(62) Division of application No. 10/372,449, filed on Feb. 25, 2003, now Pat. No. 7,074,978.

(51) Int. Cl.
*B01J 8/04* (2006.01)
*C07C 2/64* (2006.01)
*C07C 2/00* (2006.01)

(52) U.S. Cl. .................. 422/188; 585/310; 585/314; 585/315; 585/316; 585/323; 585/449

(58) Field of Classification Search .................. 422/188; 585/310, 314, 315, 316, 319, 323, 449
See application file for complete search history.

(56) References Cited

U.S. PATENT DOCUMENTS

| | | |
|---|---|---|
| 3,077,491 A | 2/1963 | Seglin et al. |
| 3,200,164 A | 8/1965 | Gerald |
| 3,205,277 A | 9/1965 | Pollitzer et al. |
| 3,428,701 A | 2/1969 | Ward |
| 3,843,739 A | 10/1974 | Harper et al. |
| 4,008,290 A | 2/1977 | Ward |

(Continued)

FOREIGN PATENT DOCUMENTS

EP  502 265  11/1991

(Continued)

OTHER PUBLICATIONS

Derwent Pub. XP-002292013, Abstract for CN 1,235,146, Nov. 17, 1999.

*Primary Examiner*—Walter D Griffin
*Assistant Examiner*—Huy-Tram Nguyen
(74) *Attorney, Agent, or Firm*—Dilworth & Barrese, LLP.

(57) ABSTRACT

A process for the production of alkylbenzene includes the steps of introducing benzene and an olefin feed into a first alkylation reaction zone in the presence of a first alkylation catalyst under first alkylation reaction conditions to produce alkylbenzene and a vapor containing unconverted olefin; absorbing the unconverted olefin into an aromatic stream containing benzene and alkylbenzene; and, introducing the aromatic stream containing absorbed olefin into a second alkylation reaction zone containing a second alkylation catalyst under second alkylation reaction conditions to convert the absorbed olefin and at least some of the benzene of the aromatic stream to alkylbenzene. The process is particularly advantageous for the alkylation of benzene with ethylene to produce ethylbenzene. About 99.9% conversion of ethylene is achieved overall, with a substantial reduction in the required catalyst.

7 Claims, 2 Drawing Sheets

U.S. PATENT DOCUMENTS

| | | | |
|---|---|---|---|
| 4,048,243 | A | 9/1977 | Ruckelshauss |
| 4,051,191 | A | 9/1977 | Ward |
| 4,083,886 | A | 4/1978 | Michalko |
| 4,169,111 | A | 9/1979 | Wight |
| 4,215,011 | A | 7/1980 | Smith, Jr. |
| 4,232,177 | A | 11/1980 | Smith, Jr. |
| 4,242,530 | A | 12/1980 | Smith, Jr. |
| 4,250,052 | A | 2/1981 | Smith, Jr. |
| 4,302,356 | A | 11/1981 | Smith, Jr. |
| 4,307,254 | A | 12/1981 | Smith, Jr. |
| 4,316,997 | A | 2/1982 | Vaughan |
| 4,371,714 | A | 2/1983 | Young |
| 4,423,254 | A | 12/1983 | Olah |
| 4,443,559 | A | 4/1984 | Smith, Jr. |
| 4,459,426 | A | 7/1984 | Inwood et al. |
| 4,469,908 | A | 9/1984 | Burress |
| 4,540,831 | A | 9/1985 | Briggs |
| 4,570,027 | A | 2/1986 | Boucher et al. |
| 4,587,370 | A | 5/1986 | DeGraff |
| 4,695,665 | A | 9/1987 | DeGraff |
| 4,849,569 | A | 7/1989 | Smith, Jr. |
| 4,857,666 | A | 8/1989 | Barger et al. |
| 4,870,222 | A | 9/1989 | Bakas et al. |
| 4,891,458 | A | 1/1990 | Innes et al. |
| 4,922,053 | A | 5/1990 | Waguespack et al. |
| 5,003,119 | A | 3/1991 | Sardina et al. |
| 5,030,786 | A | 7/1991 | Shamshoum et al. |
| 5,118,894 | A | 6/1992 | Le |
| 5,177,285 | A | 1/1993 | Van Opdorp et al. |
| 5,334,795 | A | 8/1994 | Chu et al. |
| 5,336,821 | A | 8/1994 | DeGraff et al. |
| 5,446,223 | A | 8/1995 | Smith, Jr. |
| 5,602,290 | A | 2/1997 | Fallon |
| 5,723,710 | A | 3/1998 | Gajda et al. |
| 5,856,607 | A | 1/1999 | Kim |
| 5,902,917 | A | 5/1999 | Collins et al. |
| 5,977,423 | A | 11/1999 | Netzer |
| 5,998,684 | A | 12/1999 | Ho et al. |
| 6,060,632 | A | 5/2000 | Takamatsu et al. |
| 6,096,935 | A | 8/2000 | Schulz et al. |
| 6,252,126 | B1 | 6/2001 | Netzer |
| 6,281,399 | B1 * | 8/2001 | Schulz et al. ............... 585/323 |
| 6,376,729 | B1 * | 4/2002 | Merrill et al. ............... 585/449 |
| 6,486,371 | B1 * | 11/2002 | Butler et al. ................. 585/449 |
| 6,620,387 | B1 * | 9/2003 | Sy .............................. 422/194 |
| 6,762,334 | B1 * | 7/2004 | Stewart et al. .............. 585/323 |
| 6,995,295 | B2 * | 2/2006 | Clark et al. ................. 585/449 |
| 7,074,978 | B2 * | 7/2006 | Pohl ........................... 585/449 |
| 2002/0182124 | A1 * | 12/2002 | Woodard et al. ............ 422/149 |
| 2003/0028059 | A1 * | 2/2003 | Hamper et al. .............. 585/323 |
| 2004/0167371 | A1 * | 8/2004 | Pohl ........................... 585/449 |
| 2004/0254412 | A1 * | 12/2004 | Pohl ........................... 585/449 |
| 2006/0204410 | A1 * | 9/2006 | Pohl ........................... 422/188 |
| 2006/0229479 | A1 * | 10/2006 | Pohl ........................... 585/467 |

FOREIGN PATENT DOCUMENTS

EP    0 733 608    B1    1/2000

* cited by examiner

PROCESS FOR THE PRODUCTION OF ALKYLBENZENE

CROSS REFERENCE TO RELATED APPLICATIONS

The present application is a divisional of U.S. patent application Ser. No. 10/372,449 filed Feb. 25, 2003 now U.S. Pat. No. 7,074,978, to which priority is claimed.

BACKGROUND

1. Technical Field

The present disclosure relates to an alkylation process for the production of an alkylaromatic from an olefin and an aromatic, and particularly to the production of ethylbenzene from ethylene and benzene.

2. Background of the Art

Various processes for the production of alkylbenzene by the alkylation of benzene with an olefin are known in the art. Among the most common olefins used are ethylene and propylene. The alkylation of benzene with ethylene produces ethylbenzene. The alkylation of benzene with propylene produces cumene.

Ethylbenzene is an important chemical used mostly as a precursor for the production of styrene, which is subsequently polymerized to produce polystyrene. Various methods are known for the production of ethylbenzene. Typically, benzene and ethylene are combined in an alkylation reaction in the presence of a suitable catalyst. Various alkylation catalysts are known, and commonly used catalysts include Friedel-Crafts catalysts such as aluminum or boron halides, and various zeolites.

The reaction produces, in addition to ethylbenzene, a byproduct containing polyethylbenzenes ("PEB") such as diethylbenzene, triethylbenzene and tetraethylbenzene. The polyethylbenzenes are undesirable and are usually recycled to a transalkylation reactor for conversion to ethylbenzene by reaction with benzene.

Ethylbenzene has been produced in a process wherein the alkylation reaction was performed by catalytic distillation. The zeolite catalyst is contained in specially packaged bales, and the alkylation reaction is conducted in mixed vapor-liquid phase.

U.S. Pat. No. 5,003,119 to Sardina et al., which is incorporated by reference herein, discloses a process for the manufacture of alkylbenzenes, such as ethylbenzene and cumene, wherein a feed of fresh and recycle benzene and fresh olefin are reacted in the presence of an alkylation catalyst in an alkylator having at least two reaction stages wherein each stage is adiabatic. Essentially all of the olefin is completely reacted in each stage of the alkylator. Fresh olefin is fed into each stage of the alkylator.

Up to now, for a dilute ethylene feed, 99% of the ethylene conversion has been achieved in the alkylator. This level of conversion requires a large amount of catalyst. The vent gas from the alkylator is sent to a vent absorber where the benzene is absorbed in a hydrocarbon stream (e.g., polyethylbenzenes). The ethylene contained in the vent gas was ultimately lost. It would be advantageous to have a substantially complete conversion of ethylene with a reduced overall amount of required catalyst.

SUMMARY OF THE INVENTION

A process is provided herein for the production of alkylbenzene. The process comprises the steps of (a) introducing benzene and an olefin feed into a first alkylation reaction zone in the presence of a first alkylation catalyst under first alkylation reaction conditions to produce an effluent containing alkylbenzene and an overhead stream; (b) separating the overhead stream into a liquid portion containing benzene and a vapor portion containing unconverted olefin; (c) introducing the liquid portion of the overhead stream and a stream of polyalkylbenzene into a transalkylation zone in the presence of a transalkylation catalyst under transalkylation reaction conditions to convert at least some benzene and polyalkylbenzene to alkylbenzene; (d) absorbing a major portion of the unconverted olefin in the vapor portion of the overhead stream into an aromatic stream containing benzene and alkylbenzene; and, (e) introducing said aromatic stream containing absorbed olefin into a second alkylation reaction zone containing a second alkylation catalyst under second alkylation reaction conditions to convert said absorbed olefin and at least some of the benzene of the aromatic stream to alkylbenzene. The process is particularly suited for the purpose of making ethylbenzene and requires much less catalyst than prior systems while achieving higher overall conversion of ethylene.

BRIEF DESCRIPTION OF THE DRAWINGS

Various embodiments are described herein with reference to the drawings wherein.

DETAILED DESCRIPTION OF PREFERRED EMBODIMENT(S)

The alkylation process of the present invention can be employed for alkylation of benzene with any suitable olefin, such as ethylene, propylene, and the like. However, the process herein is particularly advantageous for the production of ethylbenzene and will be described in connection with the alkylation of benzene with ethylene. It should be remembered that propylene or other olefins may also be used and are considered to be within the scope of the present invention.

The process of the present invention includes a second alkylation finishing reactor to convert substantially all of the remaining olefin carried over in the vent gas from the alkylator. This improvement prevents the loss of olefin yield and reduces the amount of catalyst required in the alkylator.

Figure 1:
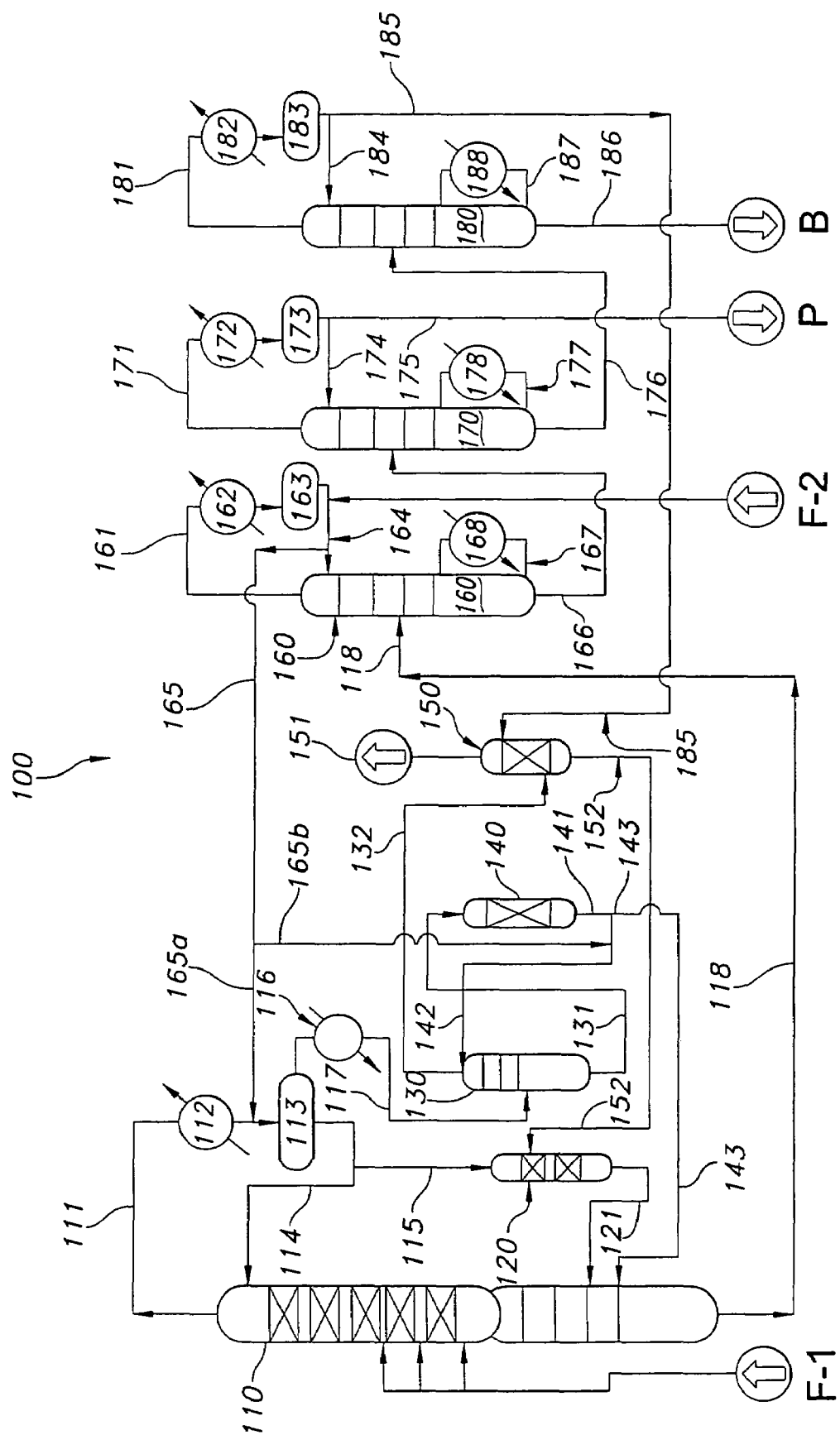
FIG. 1 is schematic flow chart of the process for producing ethylbenzene.

Referring to FIG. 1, an ethylene feed F-1 and a benzene feed F-2 are introduced into the ethylbenzene production process 100 as shown. Ethylene feed F-1 can contain 5% to 100% by volume of ethylene, and can optionally be an offgas from a refinery operation such as FCC, which generally contains about 10% to about 30% by volume of ethylene. A typical FCC offgas contains 50% to 70% methane and hydrogen, with the balance being about equal amounts of ethane and ethylene and minor amounts of other hydrocarbon components. A preferred feedstock F-1 contains 30% to 50% by volume of ethylene with the rest of the components including methane, ethane, hydrogen and other components. Optionally, the feed F-1 to the alkylator 110 can be polymer grade ethylene. Ethylene feed F-1 is sent to an alkylator 110 which is preferably a catalytic distillation column including a suitable alkylation catalyst such as one or more catalyst selected from zeolite X, zeolite Y, zeolite L, TMA Offretite, mordenite, and amorphous silica-alumina, zeolite BEA (beta), zeolite MWW, or MFI catalyst. Zeolite BEA is preferred. The catalyst is optionally contained in packaged bales.

Various types of catalytic distillation apparatus and methods and apparatus are known in the art. Alkylator 110 is mixed phase (liquid/vapor) reactor operating at alkylation reaction conditions, typically at a pressure of from about 270 psig to about 550 psig, a temperature of from about 185° C. to about 250° C., and a phenyl:ethyl ratio ranging from about 2.0 to about 3.5.

Alkylator 110 is suited to handle dilute ethylene feed and is capable of handling variations in the ethylene content and flowrate.

The feed F-1 is preferably injected at multiple points in the reactor and is contacted and dissolved in the liquid benzene introduced into the alkylator 110 via line 114 and flowing downward through the catalyst packing in the column 110. The ethylene absorbed by the benzene reacts with the benzene upon contact with the catalyst to form ethylbenzene and minor amounts of PEB. The outflow of liquid from the bottom of the alkylator 110 (i.e., the ethylbenzene-containing liquid) is sent via line 118 to distillation column 160. Column 160 separates benzene from the ethylbenzene product and heavier components. The benzene is distilled overhead as a vapor and is sent via line 161 to condenser 162 where it is liquefied and held in accumulator 163. Benzene from accumulator 163 is sent via line 164 back to column 160 as a reflux. A portion 165 of the benzene is drawn off from line 164 and is sent via line 165a to the overhead from the alkylator 110 and via line 165b to the vent absorber 130 as described more fully below. Fresh benzene feed F-2 is introduced into line 164. The fresh benzene can be fed to numerous other places in the process that are benzene rich, this is just the preferred location. The fresh benzene should be free of amines, aldehydes, ketones, and basic nitrogen compounds, which can poison the catalysts used in the process. Bottom stream 167 is recirculated back to the column 160 through reboiler 168.

A bottom stream 166 containing ethylbenzene and PEB is sent to distillation column 170. Column 170 separates the ethylbenzene product from PEB. Bottom stream 177 is recirculated back to ethylbenzene column 170 through reboiler 178. Bottom stream 176 containing PEB is sent to distillation column 180 for separation of PEB. The overhead ethylbenzene vapor stream 171 from column 170 is liquefied in condenser 172 and sent to accumulator 173. A portion of the overhead is returned to column 170 as reflux via line 174. Another portion is withdrawn via line 175 as ethylbenzene product P.

Column 180 separates the PEB (e.g., diethyl benzene) from a heavy flux oil. The bottom stream 187 is recirculated back to column 180 through reboiler 188. A portion of the bottoms is withdrawn is withdrawn via line 186 as a heavy flux oil B. Flux oil typically contains diphenylethane, tetraethylbenzene, and other high boiling components. The flux oil can be used as a fuel oil, heat transfer fluid or an absorbent. The overhead PEB vapor is liquefied in condenser 182 and sent to accumulator 183. A portion of the overhead is returned to column 180 via line 184 as a reflux. Another portion of the PEB overhead is sent via line 185 to vent stripper 150, as explained in further detail below.

Considering once again the alkylator 110, the overhead vapor 111 from the alkylator is partially liquefied by condenser 112 and sent to accumulator 113. Also received into the accumulator 113 is a portion 165a of the benzene stream 165, which is divided into portions 165a and 165b. Accordingly, accumulator 113 contains combined recycled benzene and condensed alkylator overhead as well as uncondensed vapor. A portion of the liquid from accumulator 113 is sent back to the alkylator 110 as a reflux. Another portion is sent via line 115 to transalkylator 120. Transalkylator 120 also receives a stream of PEB from vent stripper 150 via line 152. In the transalkylator 120 the benzene (from line 115) and the PEB (from line 152) react to form ethylbenzene, which is recycled back to alkylator 110 via line 121.

Transalkylator 120 contains a suitable transalkylation catalyst such as zeolite beta, zeolite Y or other suitable zeolite, and is operated under suitable transalkylation reaction conditions. Typically, transalkylation reaction conditions include a temperature of from about 185° C. to about 250° C., a pressure of from about 350 psig to about 600 psig, a space velocity of from about 3.5 to 5.0 WHSV, and a molar ratio of phenyl to ethyl of from about 2.0 to about 5.0, wherein 3.0 is preferred.

The uncondensed vapor from accumulator drum 113 is heated in heat exchanger 116 and the vapor stream containing ethylene, benzene and inerts such as ethane, methane and hydrogen is sent via line 117 to vent absorber 130 for recovery of aromatics.

Figure 2:
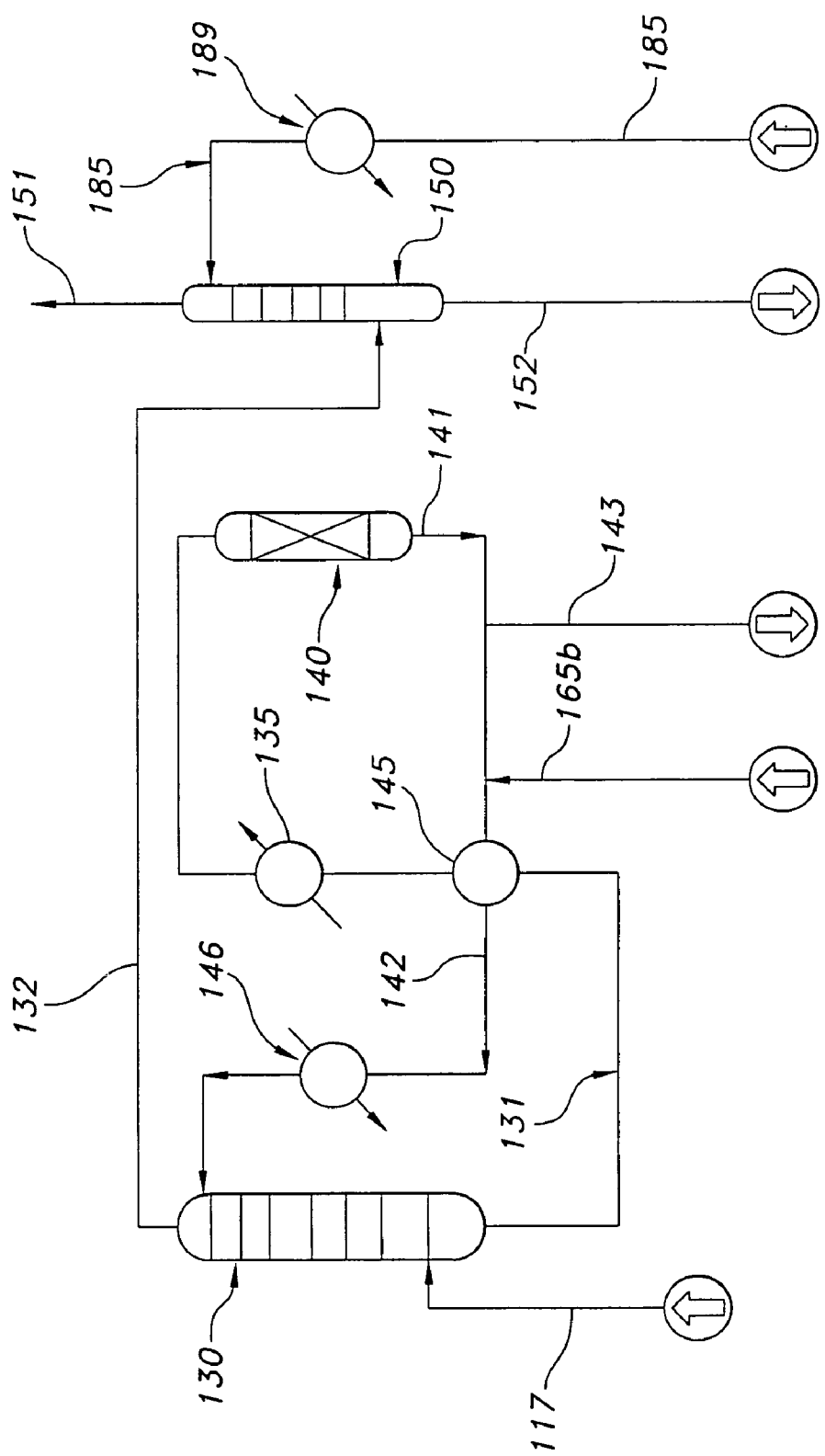
FIG. 2 is a more detailed view of a portion of the process.

Referring now to both FIG. 1 and FIG. 2, in vent absorber 130, the vapor stream flowing upward in vent absorber 130 is contacted with a downward flow of lean oil containing benzene and ethylbenzene but substantially no ethylene. The lean oil is introduced into the vent absorber via line 142. Vent absorber 130 can be a packed column or a tray column operating in countercurrent mode. Vent absorber columns are known in the art.

The lean oil dissolves almost all of the ethylene. The loss of ethylene in the overhead vapor (line 132) from the vent absorber 130 is about 1.0% of the ethylene fed to the unit (line 117). The bottoms from the vent absorber 130 containing a rich oil (i.e., with dissolved ethylene) is sent via line 131 to a finishing reactor 140 for conversion of ethylene and benzene to ethylbenzene. The rich oil stream contains at least 0.2% by weight of ethylene, preferably at least about 0.3 wt % ethylene, and more preferably at least about 1.0 wt % ethylene, and at least about 5.0 wt % ethylbenzene, preferably at least about 10 wt % ethylbenzene, and more preferably at least about 13 wt % ethylbenzene. The rich oil stream first passes through heat exchanger 145 wherein heat is transferred from the lean oil (line 142) from the finishing reactor 140 to the rich oil stream in line 131. The rich oil stream is further heated in heater 135 and sent to the finishing reactor 140.

Finishing reactor. 140 is a second alkylator which contains a fixed bed of loose catalyst, preferably zeolite Y or zeolite BEA (beta), zeolite MWW, Mordenite, or MFI catalyst and operates adiabatically in a single, liquid phase. Alkylation in the liquid phase is more efficient and requires less catalyst than alkylation in the mixed vapor/liquid phases. Conversion of ethylene in this reactor 140 is substantially complete. Finishing reactor 140 operates at a temperature of from about 200° C. to about 230° C., a pressure of from about 550 psig to about 900 psig, a phenyl:ethyl mole ratio of from about 2.0 to about 10.0. The high phenyl:ethyl mole ratio results in excellent catalyst selectivity and stability. The effluent stream 141 from the finishing reactor carriers a lean oil containing benzene and ethylbenzene. A portion of the lean oil is sent via line 143 back to the alkylator 110 to maintain the liquid inventory in the absorber system, and carries the net amount of ethylbenzene made in finishing reactor 140. A portion of the benzene from the overhead 165 of the benzene column is fed into the lean oil stream via line 165b to maintain a desired benzene concentration in the stream, which provides the desired selectivity in the finishing reactor 140. The resulting stream 142 is cooled against the effluent 131 from the vent absorber in heat exchanger 145, as stated above, and is further chilled in cooler 146 to a temperature ranging from about 6° C. to about 40° C., preferred is 12° C., whereupon it is fed to the top of the vent absorber 130.

The overhead vapor from the vent absorber 130 containing methane, ethane, hydrogen, traces of water, non-aromatics, benzene and ethylene, is sent via line 132 to the vent scrubber 150 for aromatic recovery where the upflow of vent gas is contacted with downflow of PEB from the PEB column 180. The vent scrubber 150 is operated to reject into the overhead gas (line 151) a small amount of $C_6$ non-aromatics and benzene as well as the inerts (hydrogen, methane, ethane, water, etc). The PEB stream 185 from column 180 is first chilled in a cooler 189 and then introduced at the top of the vent scrubber column 150. The scrubbed vent gas exits the vent scrubber 150 via line 151. Very little ethylene is vented from the vent scrubber 150. The overall ethylene conversion of the process is about 99.9%. The bottoms from the vent scrubber 150 containing PEB and other aromatics are sent to the transalkylator 120 via line 152 for conversion of the PEB to ethylbenzene by transalkylation with benzene.

EXAMPLE

In a system as shown in FIG. 1, a feed F-1 is introduced into alkylator 110. Table 1 below sets forth the following stream compositions. The weight percentages of the components are based on the composition of the individual streams. The alkylator 110 in this Example operates at about 90% conversion of ethylene.

TABLE 1

(Composition percentages, wt %)

| | Streams | | | | | |
|---|---|---|---|---|---|---|
| | F-1 | 111 | 118 | 117 | 115 | 131 | 151 |
| Ethylene | 55.0 | 0.75 | 0.0 | 7.35 | 0.12 | 0.40 | 0.12 |
| Benzene | 0 | 86.97 | 50.10 | 9.33 | 71.22 | 81.67 | 0.11 |
| Ethyl benzene | 0 | 2.91 | 37.50 | 0.01 | 2.97 | 13.74 | >0.01 |
| PEB[1] | 0 | 0.02 | 11.80 | 0.0 | 23.66 | 0.45 | 0.12 |
| Inerts[2] | 45.0 | 7.90 | 0.00 | 82.66 | 0.94 | 2.90 | 99.63 |
| Other[3] | 0 | 1.45 | 0.60 | 0.65 | 1.09 | 0.84 | 0.02 |

[1] Diethylbenzene, triethylbenzene, tetraethylbenzene.
[2] Hydrogen, methane, ethane, butane.
[3] $C_6$ and $C_7$ non-aromatics, toluene, cumene, butylbenzene, diphenylethane, and high boiling compounds.
111 - Alkylator 110 overhead
118 - alkylator bottoms
117 - Feed to vent absorber 130
115 - Feed to transalkylator 120
131 - Feed to second alkylator 140
151 - Overhead from vent scrubber 150

With the use of a second alkylator (140), less than about 0.1% of the ethylene originally fed to the system (in feed F-1) is vented from the vent scrubber 150. The overall conversion of ethylene is more than 99.9%.

Alkylator 110 is preferably operated at about 80% conversion, which requires less than half the catalyst as that needed to achieve 99% conversion in conventional systems with only a single alkylator operating in the mixed liquid-vapor mode. The additional catalyst required by the second alkylator, operating more efficiently in the liquid mode, is only about 5% of the amount needed by the conventional systems. The system of the present invention can achieve higher overall conversion of ethylene with about half the catalyst needed by conventional ethylbenzene production systems. This represents a considerable savings in capital and operating costs.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A system for the production of alkylbenzene comprising:
   a) first alkylator means for alkylating benzene with an olefin, wherein the first alkylator means produces an effluent containing alkylbenzene and benzene, and an overhead stream;
   b) condensing means for separating the overhead stream from the first alkylator means into a vapor stream and a liquid stream;
   c) transalkylator means for contacting the liquid stream from the first alkylator means overhead with a stream containing polyalkylbenzene to produce a transalkylator effluent containing alkylbenzene and benzene;
   d) absorber means for contacting the vapor stream from the first alkylator means overhead with a lean oil stream containing benzene and alkylbenzene to produce a rich oil stream containing benzene, alkylbenzene and unconverted olefin; and
   e) second alkylator means for converting the unconverted olefin and at least some of the benzene in the rich oil stream to produce the lean oil stream.

2. The system of claim 1 wherein the first alkylator means comprises a catalytic distillation unit.

3. The system of claim 1 wherein the absorber means comprises a packed column.

4. The system of claim 1 wherein the absorber means comprises a tray column.

5. The system of claim 1 further comprising a scrubber unit for contacting a vapor overhead from the absorber means with a downflow stream containing polyalkylbenzene.

6. The system of claim 1 further comprising distillation means for separating out benzene and alkylbenzene from the alkylator means effluent.

7. The system of claim 1 further comprising heat transfer means for transferring heat between the lean oil stream and the rich oil stream.

* * * * *